United States Patent [19]
Holmes

[11] Patent Number: 5,431,670
[45] Date of Patent: Jul. 11, 1995

[54] SURGICAL SUTURING INSTRUMENT

[75] Inventor: Russell P. Holmes, Boston, Mass.

[73] Assignee: Hol-Med Corporation, So. Easton, Mass.

[21] Appl. No.: 135,783

[22] Filed: Oct. 13, 1993

[51] Int. Cl.[6] .............................................. A61B 17/00
[52] U.S. Cl. ...................................... 606/147; 606/1; 606/139; 606/144; 606/148
[58] Field of Search .................... 606/1, 139, 144, 145, 606/147, 148, 151, 106; 600/9, 11, 13; 607/1, 116

[56] References Cited

U.S. PATENT DOCUMENTS

| | | | |
|---|---|---|---|
| 1,997,231 | 4/1935 | Plutino | 600/11 |
| 2,897,411 | 7/1959 | Brown et al. | 606/106 |
| 3,417,752 | 12/1968 | Butler | 606/147 |
| 3,664,327 | 5/1972 | Gordon et al. | 600/11 |
| 5,114,397 | 5/1992 | Tok Arek et al. | 600/11 |
| 5,201,744 | 4/1983 | Jones | 606/1 |

Primary Examiner—Peter A. Aschenbrenner
Assistant Examiner—Jeffrey A. Schmidt
Attorney, Agent, or Firm—Cesari and McKenna

[57] ABSTRACT

The suturing instrument of the present invention uses an electromagnet to position, orient and hold a needle at the end of an elongated barrel, thereby eliminating the mechanical jaws which are otherwise required. The electromagnet is contained in a barrel and extends along the length of the barrel. One end of the electromagnet emerges at the distal end of the barrel and extends to an end cap, which includes a groove for orienting the needle. Wires extending from the electromagnet and through the barrel connect to a power source which supplies current to the wires. The power source preferably has multiple power settings for supplying different levels of current. When sufficient current is applied to the electromagnet, the electromagnet attracts the needle to it, causing the needle to move to a predetermined position within the groove.

12 Claims, 1 Drawing Sheet

SURGICAL SUTURING INSTRUMENT

FIELD OF THE INVENTION

The invention relates generally to surgical instruments and, more particularly, to surgical instruments for use in endoscopic surgery.

BACKGROUND OF THE INVENTION

Endoscopic surgery is performed through a plurality of relatively small incisions, using special surgical instruments and a microscope with a tiny video camera. This type of surgery tends to reduce the length of post-surgery recovery, because the small incisions typically heal faster than do the larger incisions required in other types of surgery.

To perform endoscopic surgery, the surgeon makes a number of small incisions in the body, inserts into the incisions the surgical instruments and the microscope into the abdominal cavity through the incisions and manipulates the instruments while observing on a video screen the images transmitted by the camera.

An instrument designed for endoscopic surgery includes a thin, elongated barrel with a tool for cutting, suturing or the like at one end and a control handle for manipulating the tool at the other end. The tool is inserted into the body through one of the small incisions and the surgeon manipulates the tool by means of the handle.

A tool currently used for suturing during endoscopic surgery includes at one end movable jaws, for grasping and releasing a needle, and at the opposite end a scissor-like control handle, which is used to open and the close of the jaws and to move the needle. The surgeon grasps the needle by closing the jaws around it. She then inserts the needle into and through the tissue requiring suturing and opens the jaws to release the needle. Next, she uses the same instrument or another, similar tool to grasp the needle and pull it through the tissue. She then repeats the movements, as necessary, to complete the suturing procedure.

Throughout the suturing procedure, the surgeon has to release and re-grasp the needle a number of times. Each time the surgeon re-grasps the needle, she must be sure that it is positioned and oriented correctly within the jaws, so that she is then ready to insert the needle into and through the tissue to make another stitch. Accordingly, the surgeon must first determine the position and orientation of the needle in the jaws. This is difficult, because her only view of the needle and the instrument is via a two-dimensional image transmitted by the camera. Next, she must adjust the needle within the jaws, as necessary, which is difficult because the jaws only open and close.

Further, the surgeon must be sure that she does not drop the needle, since the needle may be difficult to locate in the transmitted image. Once a dropped needle is located, picking it up, particularly with the suturing instrument, is a challenge. Often, a special instrument, and another hand to manipulate the instrument, are required.

SUMMARY OF THE INVENTION

A suturing instrument embodying the invention uses an electromagnet to position, orient and hold a needle at the end of an elongated barrel, thereby eliminating the mechanical jaws which are otherwise required. The electromagnet is contained in the barrel and extends along the length of the barrel. One end of the electromagnet emerges at the distal end of the barrel and extends to an end cap, which includes a groove for orienting the needle. Wires extending from the electromagnet and through the barrel connect to a power source which supplies current to the wires. The power source preferably has multiple power settings for supplying different levels of current. When sufficient current is applied to the electromagnet, the electromagnet attracts the needle to it, causing the needle to move to a predetermined position within the groove.

A surgeon may use a lower power setting to attract the needle into the groove, so that the needle may be manipulated across the magnet and into a desired position within the groove. She may then use a higher setting, and thus, increase the strength of the associated magnetic field, to hold the needle in position within the groove. The surgeon may later turn the power source off, to separate the instrument from the needle. Alternatively, the surgeon may reverse the direction of the current applied to the electromagnet, to reverse the polarity of the magnet, so that the magnet repels the needle, which most likely is slightly magnetized.

To perform a suturing procedure, a surgeon first supplies current to the electromagnet and attracts the needle to the desired position and orientation at the end of the instrument. The surgeon then manipulates the instrument to insert the needle into and part way through the tissue being sutured. A back stop on the end of the groove prevents the instrument from sliding out of contact with the needle. Next, the surgeon reduces or eliminates the current applied to the electromagnet, to facilitate separation of the instrument from the needle. The surgeon may then use the same instrument or a second, similar instrument to grasp the other end of the needle and pull it through the tissue. The second instrument may include an electromagnet, such that when the second instrument pulls the needle out of the tissue, the magnet draws the needle into proper position on the end cap. Otherwise, the second instrument grasps the needle with a movable jaw.

The second instrument holds the needle until the needle is transferred to the first instrument. To transfer the needle, the two instruments are brought together and either the current applied to the second instrument is decreased or the current applied to the first instrument is increased, or both. The magnet of the first instrument draws the needle from its position on the second instrument to its previous position on the first instrument. The surgeon then, as necessary, manipulates the needle across the magnet until the sharpened end of the needle is properly aimed, and continues the suturing procedure.

Suturing instruments for use with various types of needles, for example, straight needles, curved needles, ski needles and so forth, include end caps with grooves which are oriented at various angles relative to the long axis of the barrel. The grooves are also shaped to match the shape of the needle, as necessary.

To facilitate the precise positioning of the needle in the groove, the suture end of the needle may be coated with a material which is more magnetically permeable then the needle, or the needle may include a magnet in the suture end. The suture end of the needle is then drawn into contact with the electromagnet, such that the sharpened end of the needle is appropriately aimed.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
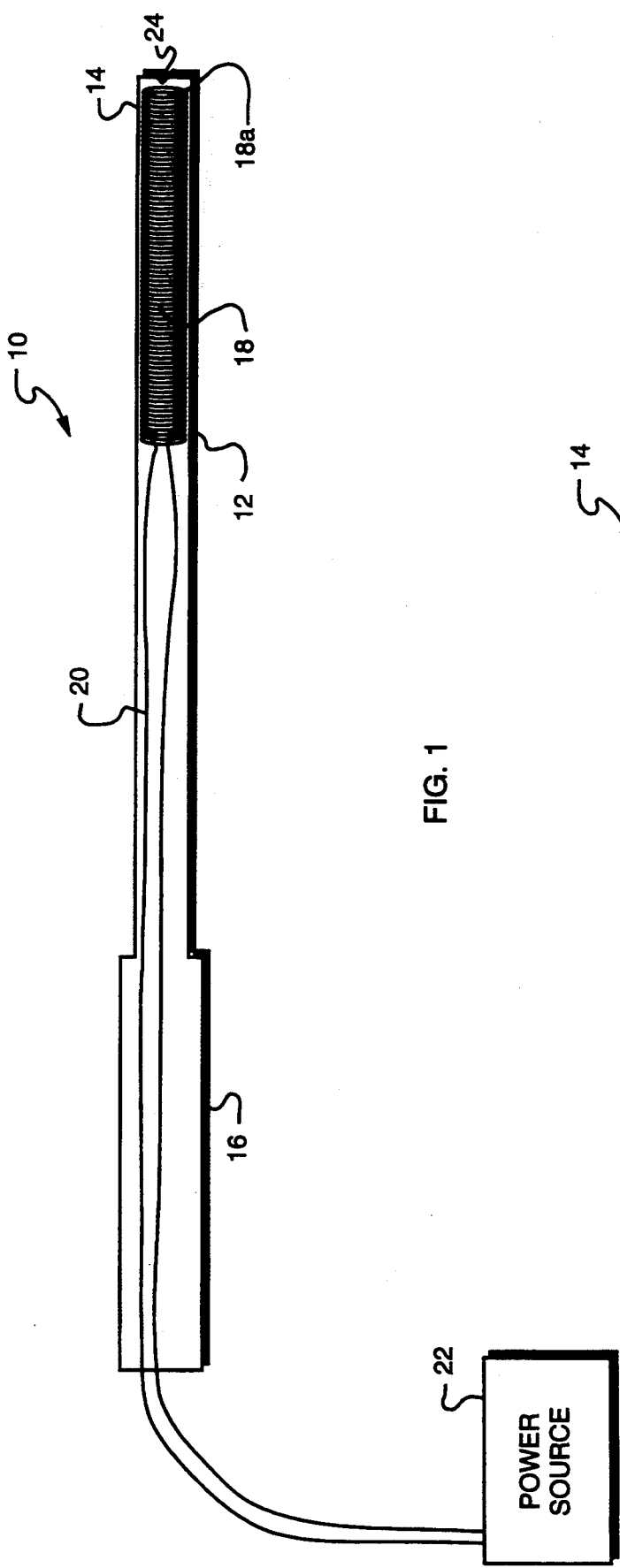
FIG. 1 is a cut away side view of a surgical instrument constructed in accordance with the invention.

FIG. 1 depicts an instrument 10 which includes an elongated, non-magnetic barrel 12 that has at one end an end cap 14 and at the opposite end an essentially straight handle 16. All or a portion of the elongated barrel is hollow and an electromagnet 18 is contained in the end of the barrel closest to the end cap 14. Wires 20 connecting the electromagnet with a power source 22 run from the electromagnet through the remainder of the barrel and exit the handle 16. The power source may include various power settings, for supplying different levels of current to the electromagnet. The power source preferably has a foot operated power adjustment mechanism (not shown).

Insulation between the non-magnetic barrel and the electromagnet isolates the electromagnet from the sides of the barrel. The remainder of the barrel is filled with sealant, which holds the magnet and the wires in place and prevents an accumulation of fluids in the barrel.

Figure 2:
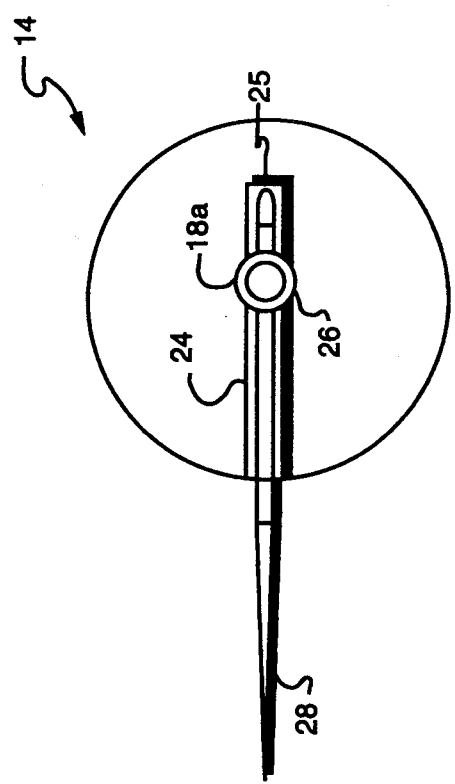
FIG. 2 is a top view of an end cap, which is part of the surgical instrument depicted in FIG. 1.

Referring also to FIG. 2, a top view the end cap 14 is shown. The end cap includes a lateral groove 24 which directs a needle 28 in a predetermined orientation relative to the long axis of the barrel 12. The needle 28 is cut-away to reveal an opening 26 in groove 24. The opening 26 accommodates one end 18a of electromagnet 18. When current is applied to the electromagnet the end 18a draws a needle laterally toward the groove 24 and pulls the needle into the groove, to properly orient the needle.

The lateral groove 24 preferably does not extend across the entire end cap. Instead, one end 25 of the groove acts essentially as a back stop. When the needle is inserted into tissue, the needle rests against the end, or back stop, 25 to prevent the instrument from sliding out of engagement with the needle. Alternatively, a back stop may be attached to the end of the groove 24.

The surgeon should approach the needle from a particular end, i.e., either the suture end or the sharpened end, depending on whether the instrument is being used to insert the needle into the tissue or pull the needle from the tissue.

The electromagnet 18 holds the needle in the groove, as long as sufficient current is applied. When the surgeon desires to separate the instrument from the needle, the surgeon decreases or shuts off the current applied to the electromagnet 18. The instrument may then be easily withdrawn from the needle. Alternatively, the surgeon may adjust the power setting of the power source to reverse the direction of the current supplied to the electromagnet. This changes the polarity of the magnet such that the needle, which most likely is slightly magnetized, is repelled.

The electromagnet 18 attracts a needle to its proper position on the end cap 14 and, as sufficient long as current is applied, it retains the needle in position such that the needle will not easily shift and/or drop off the end of the instrument. Accordingly, mechanical jaws are not required to hold the needle. Further, the surgeon is not faced with trying to locate a dropped needle by finding it within the two dimensional image transmitted by the camera.

To perform a suturing procedure, a surgeon turns on the power source 22 to supply current to the electromagnet 18, and a needle is drawn into position on the end of the barrel 12. The surgeon then increases the current supplied to the electromagnet, as necessary, and guides the needle through the tissue. If the surgeon uses two suturing instruments, she uses the second instrument to grasp the sharpened end of the needle, which is now sticking out of the other side of the tissue, and pull the needle through the tissue. As soon as the needle is grasped by the second instrument, the surgeon may either reduce the current applied to the electromagnet in the first instrument or increase the current applied to the electromagnet, if any, in the second instrument, or do both. The needle is positioned on the second instrument by the included magnet or by movable jaws. The surgeon then transfers the needle back to the first instrument by bringing the first instrument close to the second instrument and increasing the current supplied to the electromagnet in the first instrument. The electromagnet in the first instrument attracts, orients and positions the needle.

If the surgeon uses a single instrument to perform the suturing procedure, she inserts the needle into the tissue, and then reduces, eliminates or reverses the current applied to the electromagnet to release the needle. Next, she positions the instrument at the end of the needle emerging from the other side of the tissue and increases the current to the electromagnet, to attract the needle to the instrument. After pulling the needle from the tissue, the surgeon allows the needle to position itself in the groove. The surgeon then increases the current to the electromagnet, as necessary, and again inserts the needle into the tissue to continue the suturing procedure.

The needle may have, at the suture end, all embedded magnet or thin coating of material which is more magnetically permeable then the needle. Accordingly, the suture end of the needle is drawn directly to the electromagnet 18 such that the sharpened end is appropriately exposed at the open end of groove 24, without manipulation of the needle across the magnet. As discussed earlier, the direction of the current supplied to the electromagnet 18 may be reversed, to repel the magnetized needle when the instrument is being withdrawn from the needle.

The transverse groove 24 and the end cap 14 may run in any direction that positions the needle appropriately with respect to the long axis of the barrel 12. Also, the groove may be shaped, for example, curved, to accommodate shaped needles.

The instrument 10 has no moving parts to wear out. It is easier to manufacture and assemble than instruments that use movable jaws and require handles with scissor-like mechanisms to operate the jaws.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A method of performing a suturing procedure with a suturing instrument containing at one end an electromagnet, the method including the steps of:
   A. supplying current to the electromagnet;
   B. placing the end of the instrument which contains the electromagnet in proximity to a needle to attract the needle to the instrument;
   C. inserting the needle into tissue to be sutured;
   D. reducing the current;
   E. withdrawing the instrument from the needle; and
   F. pulling the needle from the tissue.

2. The method of claim 1, wherein the step of reducing the current includes setting the current to zero.

3. The method of claim 1 further including the step of grasping the needle with a second instrument, wherein the needle is grasped before the step of reducing the current is performed.

4. The method of claim 1, wherein the step of pulling the needle from the tissue includes:
   i. positioning an instrument with an electromagnet proximate to the needle;
   ii. supplying current to the electromagnet; and
   iii. drawing the needle to the electromagnet.

5. The method of claim 4, wherein the step of positioning an instrument includes positioning the same instrument used in previous steps.

6. A method of performing a suturing procedure with a suturing instrument containing at one end an electromagnet, the method including the steps of:
   A. supplying current to the electromagnet;
   B. placing the end of the instrument which contains the electromagnet in proximity to a needle to attract the needle to the instrument;
   C. inserting the needle into tissue to be sutured;
   D. reversing the current;
   E. withdrawing the instrument from the needle; and
   F. pulling the needle from the tissue.

7. The method of claim 6, wherein the step of pulling the needle from the tissue includes:
   i. positioning an instrument with an electromagnet proximate to the needle;
   ii. supplying current to the electromagnet; and
   iii. drawing the needle to the electromagnet.

8. The method of claim 7, wherein the step of positioning an instrument includes positioning the same instrument used in previous steps.

9. A surgical suturing instrument including:
   A. an elongated barrel having a first end and a second end;
   B. a handle attached to the first end of the barrel;
   C. an electromagnet positioned at the second end of the barrel; and
   D. groove means at the second end of the barrel for positioning and orienting a needle relative to a longitudinal axis of the barrel, the electromagnet attracting a needle into the groove means and holding the needle at the second end of the barrel.

10. The surgical suturing instrument of claim 9 further including an adjustable power source connected to the electromagnet to supply to the electromagnet current at varying levels.

11. The surgical suturing instrument of claim 9 wherein the groove means consists of an end cap attached to the second end of the barrel, the end cap including a transverse groove and an opening for the electromagnet.

12. The surgical suturing instrument of claim 11, wherein the end cap further includes a backstop on one end of the groove.

* * * * *